United States Patent [19]
Porchia et al.

[11] Patent Number: 5,154,086
[45] Date of Patent: Oct. 13, 1992

[54] METHOD AND APPARATUS FOR MEASURING CLOSURE FORCES AND VARIANCES THEREIN ASSOCIATED WITH RECLOSABLE THERMOPLASTIC ZIPPERED BAGS

[75] Inventors: Jose Porchia; Brian C. Dais, both of Midland, Mich.; Arnold M. Bartz, Granville; Francis D. Biel, Newark; James C. Cummins, Heath; Gary A. Douglass, Newark; James R. Hendershot, Newark; Ralph L. McCartney, Thornville; James R. Wigle, Newark, all of Ohio

[73] Assignee: Dowbrands L.P., Indianapolis, Ind.

[21] Appl. No.: 723,354

[22] Filed: Jun. 28, 1991

[51] Int. Cl.⁵ .............................................. G01N 3/08
[52] U.S. Cl. ...................................... 73/818; 73/865.9
[58] Field of Search ............ 73/818, 788, 791, 865.9, 73/792

[56] References Cited

U.S. PATENT DOCUMENTS

| | | | |
|---|---|---|---|
| 2,493,782 | 10/1945 | Schwarz | 73/9 |
| 3,199,342 | 8/1965 | Snair et al. | 73/831 |
| 3,620,071 | 6/1970 | Kelley et al. | 73/826 |
| 4,102,180 | 7/1978 | Devarakonda | 73/831 |
| 5,033,308 | 7/1991 | LeCompagnon et al. | 73/788 |

Primary Examiner—Hezron E. Williams
Assistant Examiner—Howard Wisnia

[57] ABSTRACT

An apparatus and method for measuring the tactility of a zipper of a reclosable thermoplastic zippered bag of the type described in commonly-assigned U.S. Pat. No. 5,070,584, including an opposed pair of mechanical fingers defining a gap therebetween through which the zipper is made to pass, means associated with the opposed pair of mechanical fingers for continuously measuring the resistance of the male and female profiles to being interlocked by such fingers as the zipper passes through the gap defined between such fingers, and means for recording, graphing, displaying and/or analyzing these measurements.

6 Claims, 4 Drawing Sheets

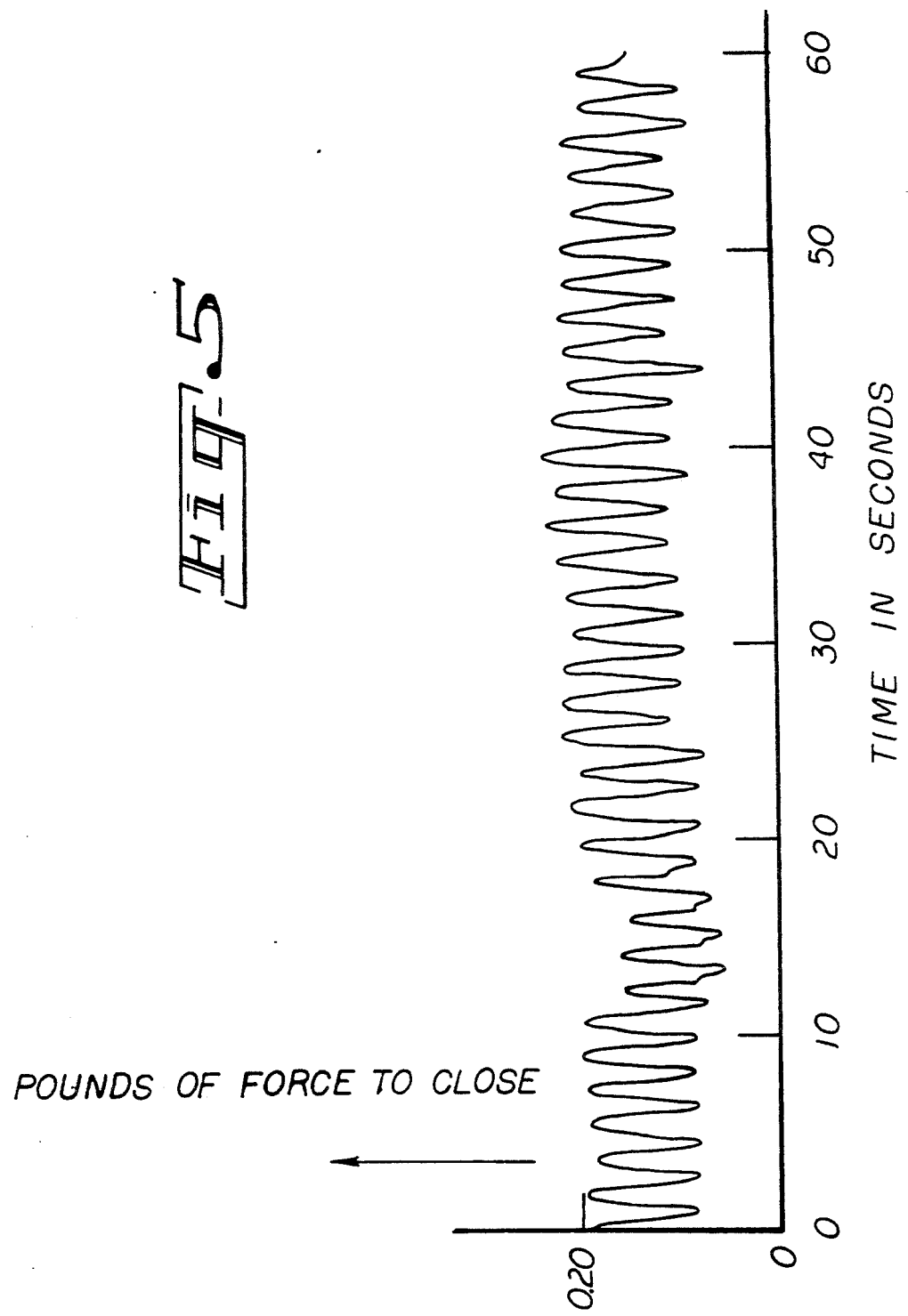

5,154,086

METHOD AND APPARATUS FOR MEASURING CLOSURE FORCES AND VARIANCES THEREIN ASSOCIATED WITH RECLOSABLE THERMOPLASTIC ZIPPERED BAGS

BACKGROUND OF THE INVENTION

The present invention relates generally to methods and apparatus for measuring certain qualities of reclosable thermoplastic zippered bags.

In particular, the present invention is concerned with reclosable thermoplastic zippered bags of the type described in commonly-assigned copending application Ser. No. 07/531,951, now issued as U.S. Pat. No. 5,070,584 (the '584 patent), such patent being hereby incorporated herein by reference.

The bags described in the '584 patent and described in much more abbreviated fashion below provide confirmation of their closure by producing a distinctive tactile and/or audible indication of the interlocking of the male and female profiles in their zippers. This tactile and/or audible indication of the proper interlocking of the male and female profiles is produced by varying the closure force required to interlock the male and female profiles over the length of the zipper. Typically the closure force is cycled intermittently over the length of the zipper between a low closure force and a high closure force, with the changes in closure force being produced in turn by making one or both of the profiles intermittently structurally discontinuous. These intermittent structural discontinuities are manifest in the form of first and second differently-shaped segments over the length of a profile part interlockable with the opposing profile. The differently-shaped segments interlock differently with corresponding portions of the opposing profile and implicate different closure forces.

The degree of certainty or assurance of closure given by the zippers in such bags is consequently directly correlated to whether perceptible variations in closure force are produced over the lengths of the zippers, but previously no devices or methods were known which could consistently measure whether certain minimum acceptable variations in closure forces were produced in the zippers. Such devices and methods would be useful from a quality control perspective for ensuring that the bags of the '584 patent provide the confirmation of closure sought by users of reclosable thermoplastic bags generally.

Such devices and methods would also be useful, however, for making measurements of the forces required to close or zip a zipper in reclosable thermoplastic zippered bags generally, since the magnitude of force required to interlock the male and female profiles of a zippered bag is also of some importance to consumers.

SUMMARY OF THE INVENTION

The present invention provides methods and apparatus for performing the functions described in the preceding paragraphs.

The apparatus of the present invention broadly comprises a) an opposed pair of mechanical fingers for effecting the interlocking of the male and female profiles of a zipper for a zippered bag over the length of the zipper and for simulating the action of a consumer's fingers in zipping the zipper, b) means associated with the opposed pair of mechanical fingers for continuously measuring the force required to zip the zipper or more precisely, the resistance of the male and female profiles to being interlocked by such fingers over the length of the profiles or profile segments, and c) means for recording and analyzing the force measurements produced by element b).

In one embodiment designed particularly for off-line measurements, the zipper of a bag to be tested is excised from the bag and is partially zipped beginning at one end of the zipper. The zipper is clamped at either end under tension sufficient to maintain alignment of the male and female profiles as they are progressively interlocked. The pair of mechanical "fingers" are positioned on opposite sides of the male and female profiles to force the male and female profiles into interlocking engagement as the zipper is drawn through a small gap defined between the two mechanical fingers, beginning adjacent the already-zipped portion of the zipper.

A load cell operatively associated with the two opposing mechanical fingers continuously and instantaneously measures the compressive force placed on the fingers by the zipper as it passes through the gap, and this force is contemporaneously graphed, displayed, recorded and/or analyzed as on a conventional strip chart recorder or through an associated computer. An indication of the necessary closure force for zipping the zipper is provided over the length of the zipper, as well as an indication of the variations in the closure force and thus of the "tactility" of the zipper.

This embodiment and other embodiments may be better understood by reference to the accompanying drawings.

BRIEF DESCRIPTION OF THE DRAWINGS

FIG. 5 is a typical graphic representation of the closure forces measured by the apparatus of FIG. 1 in the testing of a zipper of the type shown in FIG. 2 and described in the '584 patent.

DETAILED DESCRIPTION OF THE PREFERRED EMBODIMENTS

Figure 1:
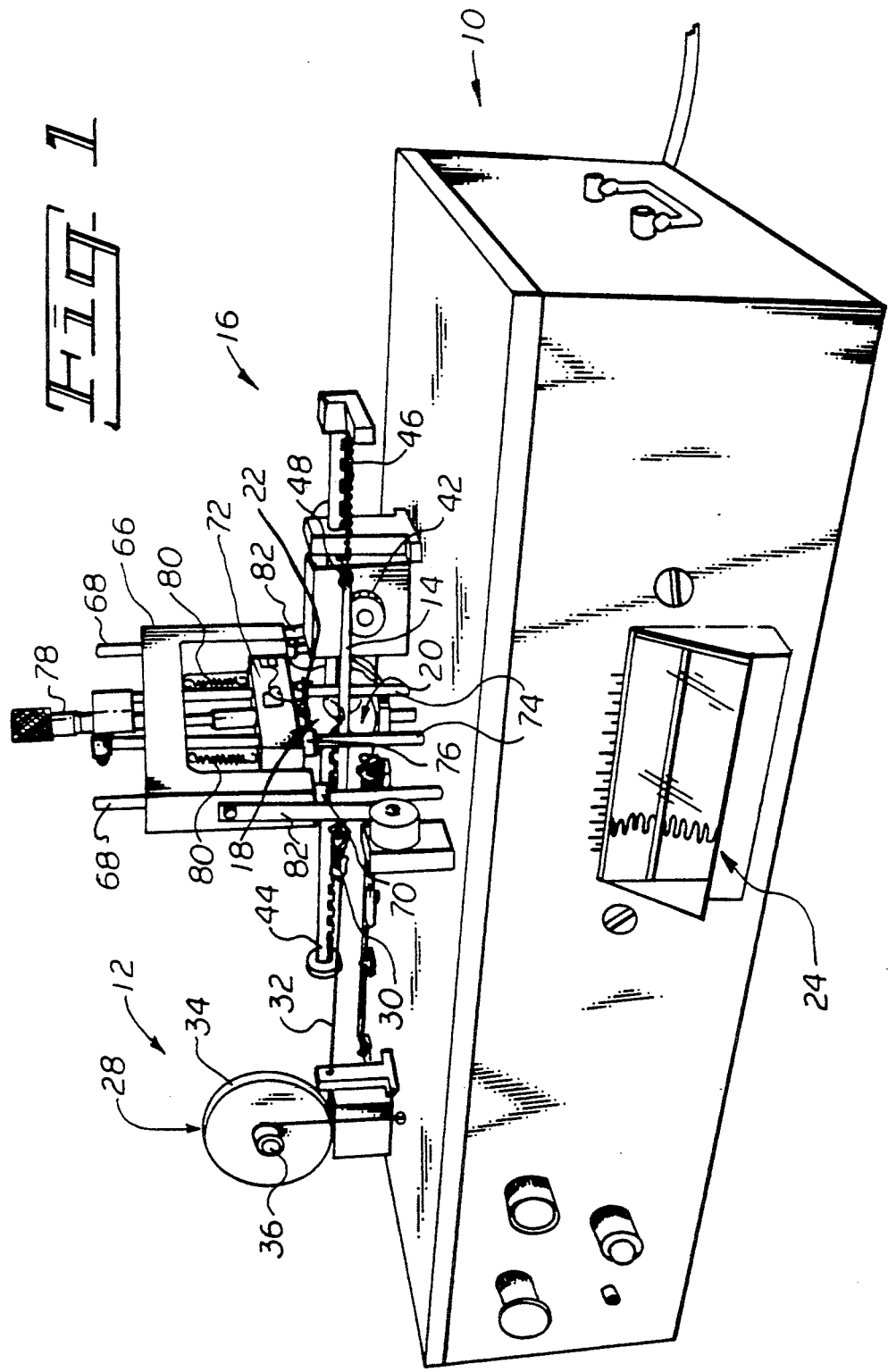
FIG. 1 is a perspective view of an apparatus of the present invention in one embodiment.
Figure 2:
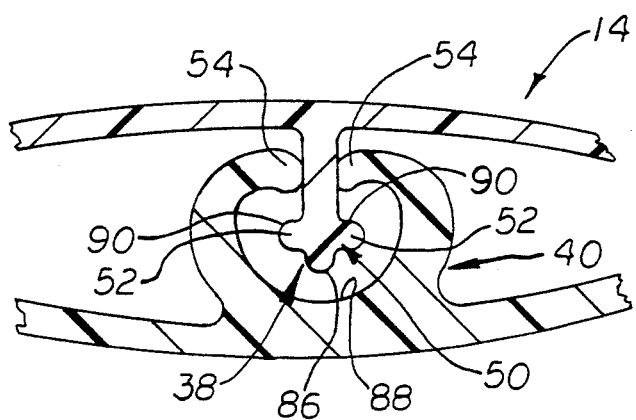
FIG. 2 is an enlarged view of a portion of a zipper made in accordance with copending application Ser. No. 07/531,951, now U.S. Pat. No. 5,070,584.
Figure 3:
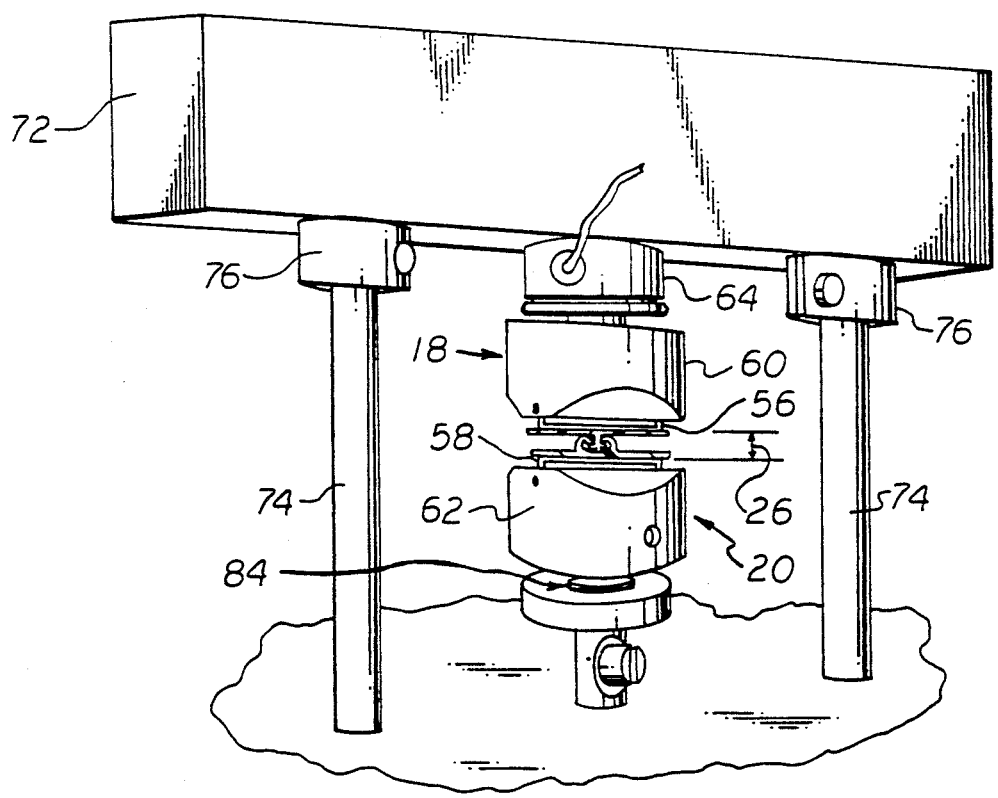
FIG. 3 is an enlarged view of a portion of the apparatus of FIG. 1, with the zipper of FIG. 2 (in cross-section) shown in position for testing.
Figure 4:
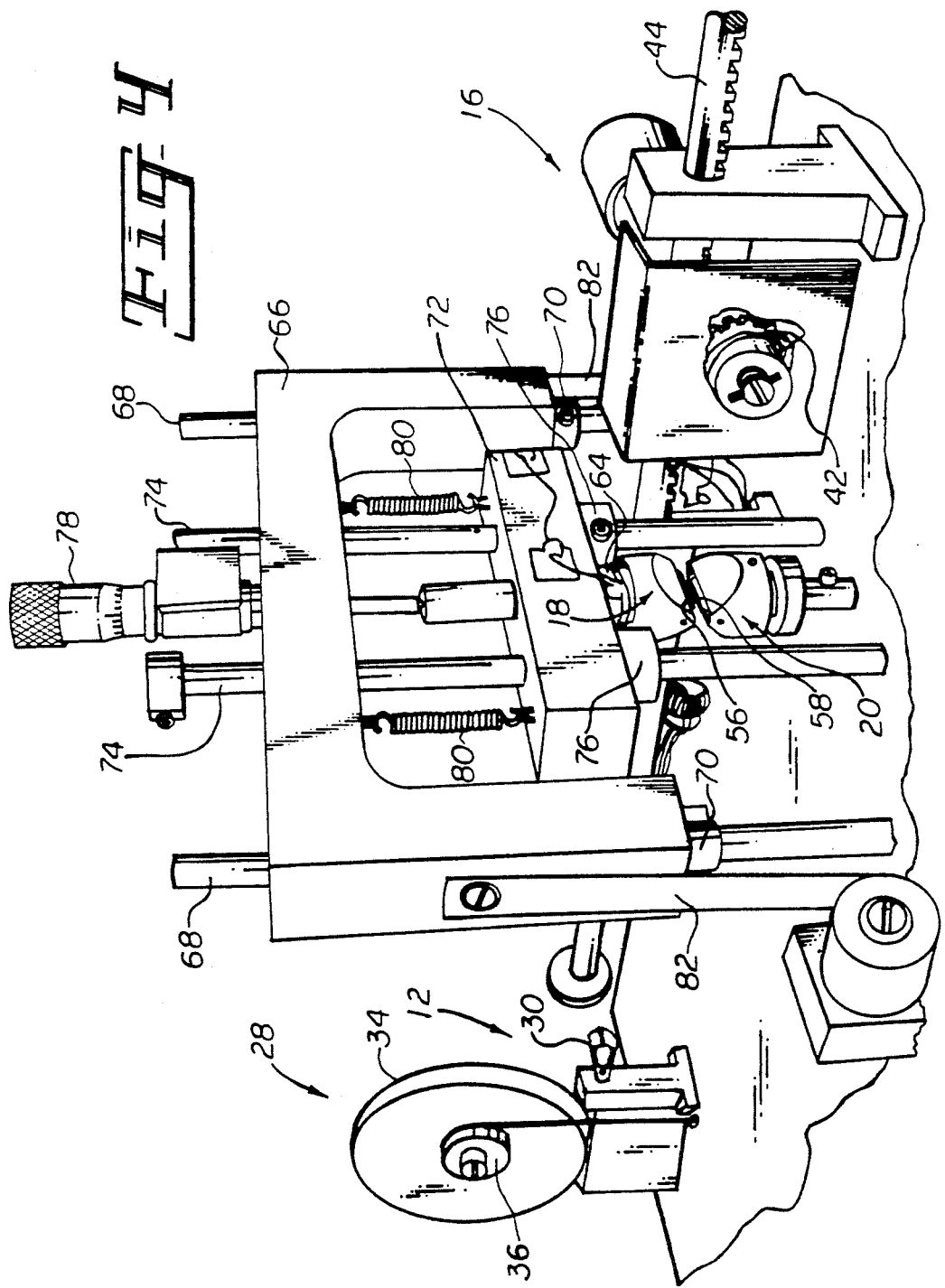
FIG. 4 is a view from the perspective of FIG. 3 of the apparatus of FIG. 1.

Referring now to the drawings, and more particularly to FIGS. 1, 3 and 4, a preferred apparatus 10 of the present invention is depicted. The apparatus 10 broadly comprises a) means 12 for holding the male and female profiles of a zipper 14 (FIGS. 2 and 3) in proper alignment for being interlocked, b) means 16 for drawing the zipper through the apparatus, c) an opposed pair of mechanical fingers 18 and 20 for effecting the interlocking of the male and female profiles over the length of the zipper 14 as the zipper 14 is drawn through the apparatus, and for thus simulating the action of a consumer's fingers in zipping the zipper, d) means 22 associated with the opposed pair of mechanical fingers 18 and 20 for continuously measuring the force required to zip the zipper 14 or more precisely, the resistance of the male and female profiles to being interlocked by such fingers over the length of the profiles or profile segments, and e) means 24 for recording and analyzing the force measurements produced by element b).

The means 12 for holding the male and female profiles of a zipper 14 in proper alignment for being interlocked as the zipper 14 is drawn through the apparatus 10, or more precisely through the gap 26 (FIGS. 3 and 4) defined between the mechanical fingers 18 and 20, consists in the apparatus 10 of a counter-weighted two-step pulley apparatus 28 and clip 30. The pulley apparatus 28 has a cable 32 which extends around a larger pulley wheel 34 and which in operation of the apparatus 10 is clipped to an end of a zipper to be tested via clip 30. A counterweight (not shown) runs off an associated smaller pulley wheel 36 to place cable 32 in just enough tension to hold the male and female profiles 38 and 40 of the zipper 14 in straight-line alignment as the zipper 14 is drawn through the gap 26 (FIGS. 2 and 3).

A limit plate (not shown) is preferably joined to the pulley wheel 34 for actuating an associated limit switch (also not shown) as the clipped end of the zipper 14 and clip 30 draw near the mechanical fingers 18 and 20. This limit switch deactivates the means 16 drawing the zipper 14 through the gap 26, and at the same time deactivates the means 24 for recording the force measurements associated with drawing the zipper 14 through the gap 26.

The means 16 for drawing the zipper 14 through the gap 26 between the mechanical fingers 18 and 20 comprises an electric motor (not shown) which drives a pinion 42. Pinion 42 intermeshes with a toothed rack 44 which extends parallel along the direction of travel of the zipper 14 through the apparatus 10. When the rack 44 is joined to the partially-interlocked end of zipper 14 via a ball and chain 46 and clip 48 as shown in FIGS. 1 and 4, the zipper 14 is thus advanced (at a generally constant rate) from the viewer's left to the viewer's right along with the rack 44 as the motor rotates pinion 42.

The purposes and interactions of the mechanical fingers 18, 20 and the means 22 for continuously measuring the resistance of the male and female profiles of zipper 14 to being interlocked as the zipper 14 is pulled through the gap 26 between fingers 18 and 20 are best understood by reference to FIGS. 2 and 3.

FIG. 2 generally illustrates one of the typically alternating segments of zipper 14 in cross-section, with the depicted segment being representative of the various segments described in the '584 patent as being characterized by indentions or structural discontinuities in a profile part interlockable with an opposite profile.

In the particular embodiment shown in FIG. 2 of the present application and in FIGS. 8 and 10 of the '584 patent, the zipper 14 is comprised of conventional rib- and groove-type, male and female profiles 38 and 40 with the head 50 of the male rib profile 38 having been intermittently mechanically deformed to possess a generally clover-shaped cross-section over segments of the profile 38. The male profile in these segments defines laterally-extending portions 52 which interact with the hooks 54 of the female groove-type profile 40 in a different manner than an undeformed head 50, and which require a different closure force than those segments of the male profile 38 having an undeformed head 50.

As has been indicated earlier, the function of the mechanical fingers 18 and 20 and the means 22 associated with such fingers is to simulate the action of a consumer's fingers in zipping a zipper 14, and to measure the resistances of the deformed sections of the male profile 38 of zipper 14 to being interlocked with groove profile 40 and of the undeformed segments of male profile 38 to being so interlocked.

Mechanical fingers 18 and 20 are thus designed to span the zipper 14 in a transverse direction, and as shown in FIG. 3 preferably comprise a pair of opposed spring wires 56 and 58 positioned on top of and below the zipper 14. These spring wires are carried on top and bottom spring wire mounts 60 and 62, respectively.

Spring wires 56 and 58 are of a sufficient diameter and strength or resiliency to compress the male and female profiles 38 and 40 of zipper 14 into interlocking engagement as the zipper 14 is drawn through the gap 26 defined between the wires 56 and 58. At the same time, the wires 56 and 58 have diameters which are less, and preferably substantially less, than the length of the deformed and undeformed segments of the male profile 38 of zipper 14.

In this way, the wires 56 and 58 are able to force the interlocking of individual segments of the male and female profiles of a zipper which are supposed to differ in the closure forces associated therewith from those associated with the segments on either side. The resistance of these individual segments of the male and female profiles to being interlocked can in this manner also be transmitted to the means 22 associated with the fingers 18 and 20 for continuously measuring such resistance. The means 22 in apparatus 10 preferably comprises a load cell 64 which is in operative communication with the wire 56 via the top spring wire mount 60. The load cell 64 continuously and individually measures the resistance of the male and female profiles of zipper 14 to being compressed by wires 56 and 58 into interlocking engagement, as the wires 56 and 58 traverse the lengths of such individual segments.

The forces sensed by the load cell 64 are communicated to means 24 for recording and/or analyzing these forces, in this case to a conventional strip chart recorder which is preferably actuated by the same control circuit as the motor driving pinion 42. For a zipper 14 of the type shown in FIG. 2 herein and in FIGS. 8 and 10 of the '584 patent, the resulting graph may preferably and typically be as shown in FIG. 5.

The "peaks" and "valleys" of FIG. 5 represent the alternately high and low closure forces required to interlock the deformed and undeformed segments of the male profile 38 with corresponding portions of the female profile 40. The magnitude of the difference between the peaks and valleys is an indication of the tactility of the zipper 14, or of the degree of bumpiness perceived by a consumer's fingers as the consumer's fingers slide along the zipper 14 and interlock the male and female profiles 38 and 40, respectively. The average height of the trace is indicative of the average closure force required of the consumer to zip the zipper 14.

Both the degree of bumpiness or tactility of a zipper and the average closure force required to zip a zipper will normally be important considerations in the proper design and manufacture of a zipper. In practical terms, a commercially acceptable zipper of the type described in the '584 patent will be designed to possess a certain degree of bumpiness or greater and a relatively low average closure force. The ability to measure and quantify these qualities by means of the present apparatus 10 is desirable for quality control purposes, and can be readily and speedily accomplished by means of a computer associated with the apparatus 10 for making the measurements described in the preceding paragraph.

It is anticipated that additional useful information about the zipper 14 may be gleaned from an examination of the symmetry and consistency of the peaks and valleys over the length of the zipper 14. Symmetric peaks, for example, are generally considered to be indicative of evenly- and well-formed clover-shaped segments of the male profile 38 of zipper 14. Inconsistently-sized peaks may be caused by inconsistencies in one or both profiles or in the deformation or alteration of the profiles.

The remainder of apparatus 10 is principally designed to protect the load cell 64 from damage associated with an undue compression of spring wire 56 and top spring wire mount 60, and can in generic terms be considered means for protecting the load cell 64 from such an undue compression.

An upper bridge assembly 66 is slidably mounted on outer support posts 68 and set collars 70, and carries a crossbar member 72 which in turn carries the load cell 64, top spring wire mount 60 and spring wire 56. Crossbar member 72 is slidably mounted on inner support posts 74 and associated set collars 76. Crossbar member 72 may be gradually and controllably moved up or down by means of a micrometer 78 positioned atop upper bridge assembly 66 and springs 80 depending from upper bridge assembly 66, with the lower limits of the crossbar member being defined by set collars 76.

Set collars 76 prevent the spring wire 56 from being compressed against spring wire 58. Sudden compressions of the spring wire 56 and damaging force placed on the load cell 64 due to the entry of clip 30 (for example, by failure of the limit switch mechanism) or a like, large object into the gap 26 are avoided by means of constant force springs 82 mounted to the upper bridge assembly 66. These constant force springs 82 are designed to allow the upper bridge assembly 66 and crossbar member 72 (with the load cell 64 and top spring wire mount 60) to move slidably upward along support posts 68 and 74 when a certain force is placed on the spring wire 56, and through load cell 64, crossbar member 72 and micrometer 78 on upper bridge assembly 66. Smaller variations in the height or thickness of items passing through the gap 26, such as variations in the heights of the male and female profiles 38 and 40 of a zipper 14, are compensated for by means of a thrust washer and wave spring assembly 84 positioned beneath the bottom spring wire mount 62.

In operation of the apparatus 10, a zipper 14 to be tested is excised from a reclosable plastic bag and the first ½ inch or so of the zipper 14 is zipped. This zipped end is clipped via clip 48 and ball and chain 46 to the toothed rack 44. The upper bridge assembly 66 and crossbar member 72 are raised as a unit, and the first zipped portion of the zipper 14 is placed on the spring wire 58. The upper bridge assembly 66 and crossbar member 72 are then carefully lowered. The opposite end of the zipper 14 is clipped under tension by clip 30, and the gap 26 narrowed by use of the micrometer 78.

The ideal initial positioning of the male and female profiles 38 and 40, shown in FIGS. 2 and 3, has the male profile 38 centered in the groove defined by female profile 40, so that the distance between the tip 86 of male rib profile 38 and the bottom 88 of the groove of female profile 40 generally equals the distance between the hooks 54 of the female profile 40 and the hooks 90 of the male profile 38. In this fashion the greatest allowance is made on average for variations in the size of one profile versus the other due to fluctuations in the conditions for making the profiles.

This maximum allowance is desirable since if the male profile were initially positioned lower in the female profile, the male profile would become fully engaged and interlocked with the female profile but would be compressed against the bottom of the female profile more often than necessary. This compression of the male profile against the bottom of the female profile would give inflated readings to the load cell 64, when the force desired to be measured is the force required to just push the male and female profiles into interlocking engagement. If on the other hand the male profile were centered higher in the female profile initially, more portions of the male and female profiles do not truly interlock on average, and the indicated closure force may reflect only the force involved in bringing the male and female profiles into contact with one another rather than in interlocking relationship.

The manner in which this initial positioning of the male and female profiles is achieved involves using the micrometer to reduce the gap 26 so that the male profile in the already-zipped portion of zipper 14 bottoms out in the female profile (marked by a sudden increase in the measured force by load cell 64, as perhaps displayed digitally), and then backing the male profile out a suitable distance based on the shape and dimensions of the male and female profiles.

The motor driving pinion 42 is then actuated along with the strip chart recorder or other recording means, and the measurements from the load cell 64 continuously monitored. The limit plate and limit switch associated with the two-step pulley apparatus 28 stop the motor and strip chart recorder when the zipper 14 has been substantially completely zipped. The bridge assembly 66 and crossbar member 72 are raised as a unit, and the zipper is unclipped at both ends and removed from the apparatus 10. The bridge assembly 66 and crossbar member 72 are lowered back into position, and the toothed rack 44 is manually returned to its starting position for receiving the next zipper to be tested.

It will be appreciated that while preferred embodiments of the present invention have been described herein, numerous variations on these embodiments are possible which are nevertheless within the scope of the present invention as more fully defined by the claims which follow.

For example, while a load cell has been described for continuously measuring the closure force variations over the length of a zipper as taught in the '584 patent, it may be preferable to employ an accelerometer in place of the load cell for measuring the vibratory feel indirectly produced by these variations in closure force. The use of an accelerometer may permit the apparatus to be operated more quickly than with a load cell, and may prove to be a more direct measure of the tactility of a given zipper.

In the same vein, it is contemplated that other conventional means for recording, displaying, graphing and/or analyzing the measurements produced by the load cell or accelerometer may be conveniently employed, as well as other means for drawing the zipper through the apparatus and other conventional means for holding the male and female profiles in proper alignment for being interlocked in the apparatus.

What is claimed is:

1. An apparatus for measuring the variances in closure force between adjacent segments of a segmented zipper of a reclosable thermoplastic zippered bag having interlockable male and female zipper profiles, comprising:

an opposed pair of mechanical fingers defining a gap therebetween through which the zipper passes, wherein the gap is dimensioned so as to force the male profile and female profile of the zipper into interlocking engagement, and wherein at least one of the male and female profiles is comprised of two or more differently-shaped segments;

means associated with the opposed pair of mechanical fingers for continuously measuring the resistance of the male and female profiles to being interlocked by such fingers as the zipper passes through the gap defined between such fingers: and means for recording, graphing, and displaying the measurements produced by the means for measuring the resistance of the male and female profiles to being interlocked.

2. An apparatus as defined in claim 1, wherein the pair of mechanical fingers comprises a pair of opposed thin spring wires which extend transversely to a zipper to be tested, and whose diameters are smaller than the length of each of the two or more differently shaped segments.

3. An apparatus as defined in claim 1, wherein the means for continuously measuring the resistance of the male and female profiles to being interlocked by said opposed pair of mechanical fingers comprises a compression load cell.

4. An apparatus as defined in claims 1, 2 or 3, further comprising means for drawing the zipper through the gap defined between the opposed pair of mechanical fingers.

5. An apparatus as defined in claims 1, 2 or 3, further comprising means for holding the male and female profiles of the zipper in proper alignment for being interlocked as the zipper passes through the gap defined between the opposed pair of mechanical fingers.

6. An apparatus for measuring the variances in closure force between adjacent segments of a segmented zipper of a reclosable thermoplastic zippered bag having interlockable male and female zipper profiles, comprising:

an opposed pair of mechanical fingers defining a gap therebetween through which the zipper passes, wherein the gap is dimensioned so as to force the male profile and female profile of the zipper into interlocking engagement, and wherein at least one of the male and female profiles is comprised of two or more differently-shaped segments:

means for drawing the zipper through the gap defined between the opposed pair of mechanical fingers:

means for holding the male and female profiles of the zipper in proper alignment for being interlocked as the zipper is drawn through the opposed pair of mechanical fingers:

means associated with the opposed pair of mechanical fingers for continuously measuring the resistance of the male and female profiles to being interlocked by such fingers as the zipper passes through the gap defined between such fingers: and means for recording, graphing, and displaying the measurements produced by the means for measuring the resistance of the male and female profiles to being interlocked.

* * * * *